(12) United States Patent
Denyer et al.

(10) Patent No.: US 10,130,779 B2
(45) Date of Patent: Nov. 20, 2018

(54) SYSTEM AND METHOD OF REMOTELY MONITORING AND/OR MANAGING THE TREATMENT OF A PLURALITY OF SUBJECTS WITH AEROSOLIZED MEDICAMENT

(75) Inventors: Jonathan S. H. Denyer, Chichester (GB); Anthony Dyche, Hayling Island (GB); Ivan Richard Prince, Chichester (GB)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1049 days.

(21) Appl. No.: 13/390,215

(22) PCT Filed: Jul. 13, 2010

(86) PCT No.: PCT/IB2010/053206
§ 371 (c)(1),
(2), (4) Date: Feb. 13, 2012

(87) PCT Pub. No.: WO2011/021118
PCT Pub. Date: Feb. 24, 2011

(65) Prior Publication Data
US 2012/0143073 A1 Jun. 7, 2012

Related U.S. Application Data

(60) Provisional application No. 61/234,264, filed on Aug. 15, 2009.

(51) Int. Cl.
*A61B 5/08* (2006.01)
*A61M 11/00* (2006.01)
(Continued)

(52) U.S. Cl.
CPC ............ *A61M 11/00* (2013.01); *A61B 5/0871* (2013.01); *A61B 5/743* (2013.01); *A61B 5/746* (2013.01);
(Continued)

(58) Field of Classification Search
CPC ........ H04J 11/004; H04B 1/525; H04L 5/002; A61B 5/091; A61B 5/087
(Continued)

(56) References Cited

U.S. PATENT DOCUMENTS 4,984,158 A * 1/1991 Hillsman ............... A61B 5/087
128/200.14
5,167,506 A * 12/1992 Kilis ...................... G09B 23/28
128/200.14
(Continued)

FOREIGN PATENT DOCUMENTS

EP 1525893 A2 4/2005
JP 2007181724 A 7/2007
(Continued)

OTHER PUBLICATIONS

Paul S. McNamara et al; "Open Adherence Monitoring Using Routine Data Download From an Adaptive Aerosol Delivery Nebuliser in Children with Cystic Fibrosis", Journal of Cystic Fibrosis, 2009, pp. 1-6.
(Continued)

*Primary Examiner* — Jacqueline Cheng
*Assistant Examiner* — Tho Tran
(74) *Attorney, Agent, or Firm* — Michael W. Haas

(57) ABSTRACT

Therapy regimes of a plurality of subjects are remotely monitored and/or managed, wherein the therapy regimes include reception of aerosolized medicament. This enables users such as medical care providers, researchers, clinic administrators, and/or other users to monitor and/or manage
(Continued)

the therapy regimes of the plurality of subjects through a centralized access point. This reduces physical requirements of proximity for the users and/or the subjects, alleviates the administrative the burden placed on the users to manage and/or monitor individual therapy regimes, and/or provides other enhancements over convention systems.

21 Claims, 11 Drawing Sheets

(51) Int. Cl.
    *A61B 5/087*     (2006.01)
    *A61M 15/00*     (2006.01)
    *G06F 19/00*     (2018.01)
    *A61B 5/00*     (2006.01)
    *A61B 5/091*     (2006.01)
    *A61M 16/00*     (2006.01)

(52) U.S. Cl.
    CPC .......... *A61M 15/009* (2013.01); *G06F 19/00* (2013.01); *G06F 19/3462* (2013.01); *A61B 5/0002* (2013.01); *A61B 5/091* (2013.01); *A61B 5/744* (2013.01); *A61M 2016/0039* (2013.01); *A61M 2202/064* (2013.01); *A61M 2205/18* (2013.01); *A61M 2205/3561* (2013.01); *A61M 2205/3584* (2013.01); *A61M 2205/502* (2013.01)

(58) Field of Classification Search
    USPC ........................................................ 600/529
    See application file for complete search history.

(56) References Cited

U.S. PATENT DOCUMENTS

| | | | | | |
|---|---|---|---|---|---|
| 5,333,106 | A | * | 7/1994 | Lanpher | G09B 5/02 128/200.12 |
| 5,394,866 | A | * | 3/1995 | Ritson | A61M 15/00 128/200.14 |
| 5,404,871 | A | * | 4/1995 | Goodman | A61M 15/00 128/200.14 |
| 5,608,647 | A | * | 3/1997 | Rubsamen | A61M 15/0091 128/204.18 |
| 5,839,429 | A | * | 11/1998 | Marnfeldt | A61M 15/00 128/200.14 |
| 6,131,567 | A | * | 10/2000 | Gonda | A61K 9/007 128/200.14 |
| 6,162,183 | A | * | 12/2000 | Hoover | A61B 5/1135 600/534 |
| 6,980,958 | B1 | | 12/2005 | Surwit et al. | |
| 7,451,760 | B2 | | 11/2008 | Denyer et al. | |
| 7,748,382 | B2 | | 7/2010 | Denyer et al. | |
| 2003/0098022 | A1 | | 5/2003 | Nakao et al. | |
| 2003/0221687 | A1 | | 12/2003 | Kaigler | |
| 2004/0158349 | A1 | | 8/2004 | Bonney | |
| 2004/0172283 | A1 | * | 9/2004 | Vanderveen | G06F 19/323 705/2 |
| 2004/0187869 | A1 | * | 9/2004 | Bjorndal | A61B 5/087 128/203.15 |
| 2005/0172958 | A1 | | 8/2005 | Singer | |
| 2006/0243277 | A1 | | 11/2006 | Denyer et al. | |
| 2007/0168461 | A1 | | 7/2007 | Moore | |
| 2008/0047553 | A1 | | 2/2008 | Denyer et al. | |
| 2009/0025718 | A1 | | 1/2009 | Denyer et al. | |
| 2009/0234240 | A1 | * | 9/2009 | Kuenzler et al. | 600/529 |
| 2012/0304987 | A1 | | 12/2012 | Denyer et al. | |
| 2017/0007494 | A1 | * | 1/2017 | Rock | A61H 9/0078 |

FOREIGN PATENT DOCUMENTS

| | | |
|---|---|---|
| WO | 199312823 | 7/1993 |
| WO | 200130231 A2 | 5/2001 |
| WO | 2004030509 A2 | 4/2004 |
| WO | 2004045689 A1 | 6/2004 |
| WO | 2009013504 A2 | 1/2009 |

OTHER PUBLICATIONS

"Treatment Analysis Model", Respironics, Inc Analysis Download, Jan. 4, 2009, pp. 1-3 http://www/bdci.co.uk/dataanalyser1//generatedreports/aiiiz03c.omg.htm.

Medical Diagnostic and Treatment Module for Advanced Patient Management System.

Anonymous, "Personal Health Monitoring Web Service Network", September 2009.

Mc Namara et al, "Open Adherence Monitoring Using Routine Data Download From an Adaptive Aerosol Delivery Nebuliser in Children With Cystic Fibrosis", Journal of Cystic Fibrosis, Vo. 8, 2009, pp. 258-263.

* cited by examiner

SYSTEM AND METHOD OF REMOTELY MONITORING AND/OR MANAGING THE TREATMENT OF A PLURALITY OF SUBJECTS WITH AEROSOLIZED MEDICAMENT

The invention relates to remotely monitoring and/or managing the therapy of a plurality of subjects, wherein the therapy comprises the delivery of aerosolized medicament.

Drug delivery devices configured to deliver aerosolized medicament to subjects are known. Typically, subjects must be trained to inhale properly during therapy. This training usually takes place in a clinical setting and is not available to subjects at home. Further, therapy that takes place at home is not generally monitored by caregivers and/or researchers in real-time or near real-time to determine whether a subject should be retrained.

One aspect of the invention relates to a system configured to remotely monitor the therapy of a plurality of subjects, wherein the therapy includes the delivery of aerosolized medicament. In one embodiment, the system comprises a server comprising one or more processors configured to execute computer program modules, the computer program modules comprising an information acquisition module, a threshold module, and a monitor module. The information acquisition module is configured to obtain, over a communications network, therapy information for a plurality of subjects, wherein the plurality of subjects comprise at least a first subject and a second subject, and wherein therapy information for a given subject includes information related to a respiratory capacity of the given subject and information conveying one or more breathing parameters of the respiration of the given subject during the delivery of aerosolized medicament. The threshold module is configured to set one or more thresholds for a first breathing parameter for the first subject based on information related to the respiratory capacity of the first subject obtained by the information acquisition module, and to set one or more thresholds for the first breathing parameter for the second subject based on information related to the respiratory capacity of the second subject obtained by the information acquisition module. The monitor module is configured to monitor the therapy received by the first subject by comparing the first breathing parameter of the first subject during delivery of aerosolized medicament, as conveyed by the therapy information for the first subject, with the one or more thresholds for the first breathing parameter for the first subject, and to monitor the therapy received by the second subject by comparing the first breathing parameter of the second subject during the delivery of aerosolized medicament, as conveyed by the therapy information for the second subject, with the one or more thresholds for the first breathing parameter for the second subject.

Another aspect of the invention relates to a computer implemented method of remotely monitoring the therapy of a plurality of subjects, wherein the therapy includes the delivery of aerosolized medicament, and wherein method is implemented by a server comprising one or more processors configured to execute one or more computer program modules. In one embodiment, the method comprises executing one or more computer program modules on the one or more processors of the server to obtain, over a communications network, therapy information for a plurality of subjects, wherein the plurality of subjects comprise at least a first subject and a second subject, and wherein therapy information for a given subject includes information related to a respiratory capacity of the given subject and information conveying one or more breathing parameters of the respiration of the given subject during the delivery of aerosolized medicament; executing one or more computer program modules on the one or more processors of the server to set one or more thresholds for a first breathing parameter for the first subject based on the obtained information related to the respiratory capacity of the first subject; executing one or more computer program modules on the one or more processors of the server to set one or more thresholds for the first breathing parameter for the second subject based on the obtained information related to the respiratory capacity of the second subject; executing one or more computer program modules on the one or more processors of the server to monitor the therapy received by the first subject by comparing the first breathing parameter of the first subject during delivery of aerosolized medicament, as conveyed by the therapy information for the first subject, with the one or more thresholds for the first breathing parameter for the first subject; and executing one or more computer program modules on the one or more processors of the server to monitor the therapy received by the second subject by comparing the first breathing parameter of the second subject during the delivery of aerosolized medicament, as conveyed by the therapy information for the second subject, with the one or more thresholds for the first breathing parameter for the second subject.

Another aspect of the invention relates to a system configured to remotely monitor the therapy of a plurality of subjects, wherein the therapy includes the delivery of aerosolized medicament. In one embodiment, the system comprises means for obtaining, over a communications network, therapy information for a plurality of subjects, wherein the plurality of subjects comprise a first subject and a second subject, and wherein therapy information for a given subject includes information related to a respiratory capacity of the given subject and information conveying one or more breathing parameters of the respiration of the given subject during the delivery of aerosolized medicament; means for setting one or more thresholds for a first breathing parameter for the first subject based on the obtained information related to the respiratory capacity of the first subject; means for setting one or more thresholds for the first breathing parameter for the second subject based on the obtained information related to the respiratory capacity of the second subject; means for monitoring the therapy received by the first subject by comparing the first breathing parameter of the first subject during delivery of aerosolized medicament, as conveyed by the therapy information for the first subject, with the one or more thresholds for the first breathing parameter for the first subject; and means for monitoring the therapy received by the second subject by comparing the first breathing parameter of the second subject during the delivery of aerosolized medicament, as conveyed by the therapy information for the second subject, with the one or more thresholds for the first breathing parameter for the second subject.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. In one embodiment of the invention, the structural components illustrated herein are drawn to scale. It is to be expressly understood, however, that the drawings are for the purpose of illustration and description only and are not a limitation of the invention. In addition, it should be appreciated that structural features shown or described in any one embodiment herein can be used in other embodiments as well. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

Figure 1:
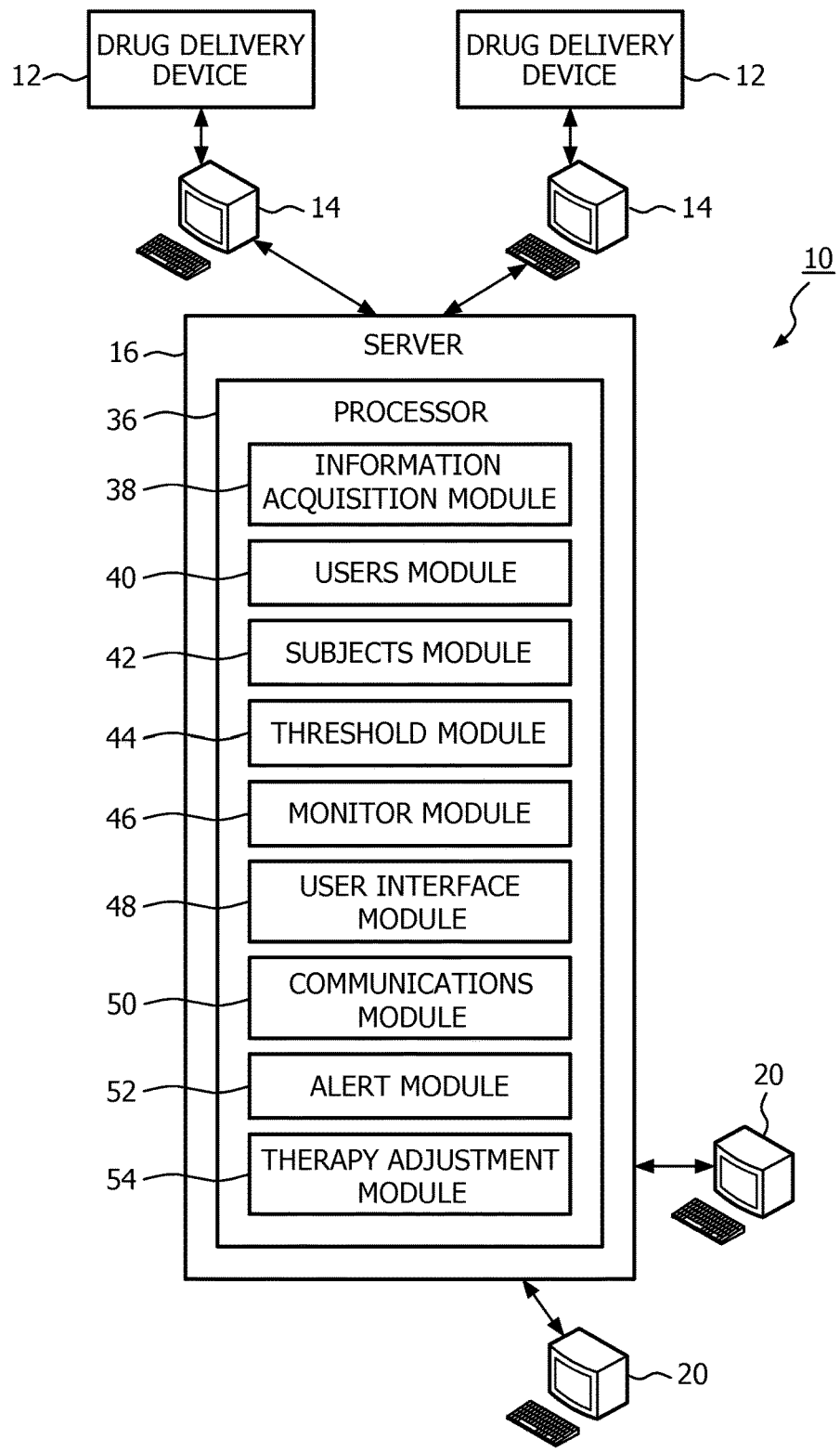
FIG. 1 illustrates a system configured to remotely monitor and/or manage therapy regimes of a plurality of subjects, according to one or more embodiments of the invention.

FIG. 1 illustrates a system 10 configured to remotely monitor and/or manage therapy regimes of a plurality of subjects, wherein the therapy regimes include reception of aerosolized medicament. System 10 enables users such as medical care providers, researchers, clinic administrators, and/or other users to monitor and/or manage the therapy regimes of the plurality of subjects through a centralized access point. This reduces physical requirements of proximity for the users and/or the subjects, alleviates the administrative the burden placed on the users to manage and/or monitor individual therapy regimes, and/or provides other enhancements over convention systems. In one embodiment, system 10 includes a plurality of drug delivery devices 12, a plurality of client computing platforms 14 associated with the plurality of subjects, a server 16, one or more client computing platforms 20 associated with one or more users of system 10, and/or other components.

The drug delivery devices 12 are configured to deliver aerosolized medicament to the subjects. For example, drug delivery devices 12 may include one or more of a nebulizer, a metered dose inhaler, a metered dose inhaler spacer, a dry powder inhaler, and/or other devices capable of delivering aerosolized medicament. One or more of drug delivery devices 12 may be configured for use in a clinical setting, in a home setting, or both. Typically, a given one of drug delivery devices 12 is considered to be associated with a specific subject, and therapy information originating from the given one of drug delivery devices 12 is assumed to be relevant to the subject associated therewith. However, this should not be viewed as limiting.

The client computing platforms 14 may include one or more of a laptop computer, a desktop computer, a netbook, a smartphone, and/or other client computing platforms. The client computing platform 14 may include one or more processors configured to execute one or more computer programming modules. At least some of the one or more computer programming modules executed on the one or more processors of client computing platform 14 include software modules associated with a software application that provides the functionality attributed herein to client computing platform 14. These software modules are stored on electronic storage media that is accessible to the one or more processors of client computing platform 14.

Each client computing platform 14 is, at least intermittently, communicatively coupled with a corresponding one of drug delivery devices 12 to obtain information therefrom and/or provide instructions or other communications thereto. This communication may be accomplished, for example, via a wireless connection (e.g., Bluetooth, WiFi, infrared, WiMax, and/or other wireless connection), and/or wired connection (e.g., USB, FireWire, etc.). These communications may include relatively short data uploads (e.g., "synching") that are instigated by determinations by a client computing platform 14 that the corresponding drug delivery device 12 is currently linked (e.g., via wireless media), and are executed in the background on client computing platforms 14 (without substantial disruption to other processes and/or applications being executed thereon). In one embodiment, communications between client computing platform 14 and drug delivery device 12 include more dedicated sessions in which processes executed on the client computing platform 14 related to the communication with client computing platform 14 are given a higher priority, and/or at least a portion of a display associated with the client computing platform 14 provides a graphical user interface associated with the use and/or functionality of drug delivery device 12 in real-time or near real-time.

The information received on client computing platform 14 from drug delivery device 12 may include, for instance, downloads of therapy information. The therapy information may include, for example, one or more of a total aerosol actuation time during one or more therapy sessions, a total amount of time the subject spent inhaling during one or more therapy sessions, a total amount of time the patient spent exhaling during one or more therapy sessions, information related to the power level at which drug delivery device 12 was operated during therapy, breathing parameters (e.g., peak flow, tidal volume, number of breaths, a timing and/or frequency of breathing, etc.) during one or more therapy sessions, and/or other therapy information.

The drug delivery device 12 and/or client computing platform 14 are configured to evaluate one or more of the parameters of the breathing of the subject. For example, client computing platform 14 and/or drug delivery device 12 may be configured to evaluate the respiratory capacity of the subject. Evaluations of respiratory capacity may be made by any of a variety of different techniques. As used herein, respiratory capacity refers to the inhalation volume measured from the end of a normal tidal exhalation to maximum lung capacity.

Evaluation of respiratory capacity by drug delivery device 12 and/or client computing platform 14 may include evaluations made by drug delivery device 12 during delivery of medicament to the subject. For example, in U.S. patent application Ser. No. 10/535,597, which is hereby incorporated into this reference in its entirety, a technique whereby a drug delivery device can evaluate the respiratory capacity of a subject is described. According to this technique, subject inhalation from a drug delivery device 12 that is delivering aerosolized medicament is controlled to approximately 20 l/min., and the subject inhales until a signal from the drug delivery device 12 indicating that a target inhalation time has been reached. This inhalation time is intended to result in an inhalation at the regulated rate (e.g., about 20 l/min.) of about 80% of the respiratory capacity of the subject.

Figure 2:
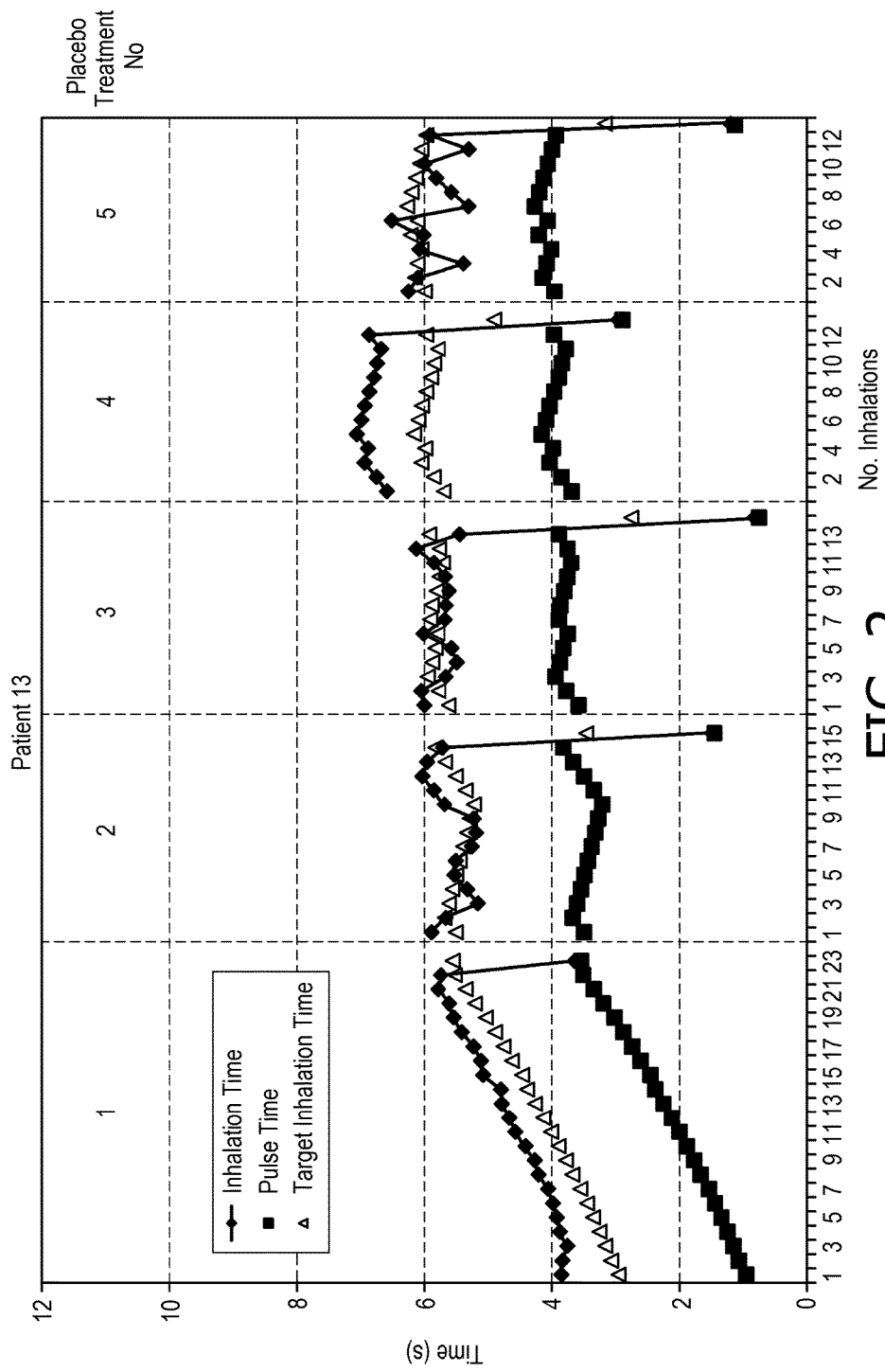
FIG. 2 illustrates a plot showing the target inhalation times and actual inhalation times (e.g., target inhalation time plus response time) for a subject over a series of breaths in each of 5 separate therapy sessions, in accordance with one or more embodiments of the invention.

At the commencement of a therapy session, the target inhalation time is a predetermined amount of time (e.g., determined based on a previous therapy session, as a device default, as a setting configured by a caregiver and/or the subject, etc.). Upon delivering the signal to the subject that the target inhalation time has been reached, drug delivery device 12 then measures the response time of the subject of the subject from the generation of the signal to the actual stoppage of inhalation. This response time will tend to be relatively long if the subject's inhalation is substantially smaller than the subject's respiratory capacity, and will tend to become shorter as the target inhalation time becomes closer to the subject's respiratory capacity. Based on the measured response time, an estimation of respiratory capacity can be made. In one embodiment, the target inhalation time is adjusted by drug delivery device 12 dynamically during individual therapy sessions based on measured response times. The measured response times and/or the target inhalation times that are determined from the response times are transmitted from drug delivery device 12 to client computing platform 14. By way of example, FIG. 2 shows a plot showing the target inhalation times and actual inhalation times (e.g., target inhalation time plus response time) for a subject over a series of breaths in each of 5 separate therapy sessions.

Returning to FIG. 1, evaluation of respiratory capacity by drug delivery device 12 and/or client computing platform 14 may include evaluations of respiratory capacity that are made by drug delivery device 12 and/or client computing platform 14 independent from the delivery of aerosolized medicament. For example, in one embodiment, drug delivery device 12 and client computing platform 14 cooperate to evaluate respiratory capacity of the subject during one or more training sessions in which the subject is taught how to breath effectively during therapy. In this embodiment, during a training session drug delivery device 12 and client computing platform 14 may be communicatively linked, and measurements of respiration parameters on drug delivery device 12 may be conveyed to client computing platform 14 in real-time or near real-time so that a graphical user interface can be provided to the subject that gives the subject feedback on the current breath.

Figure 3:
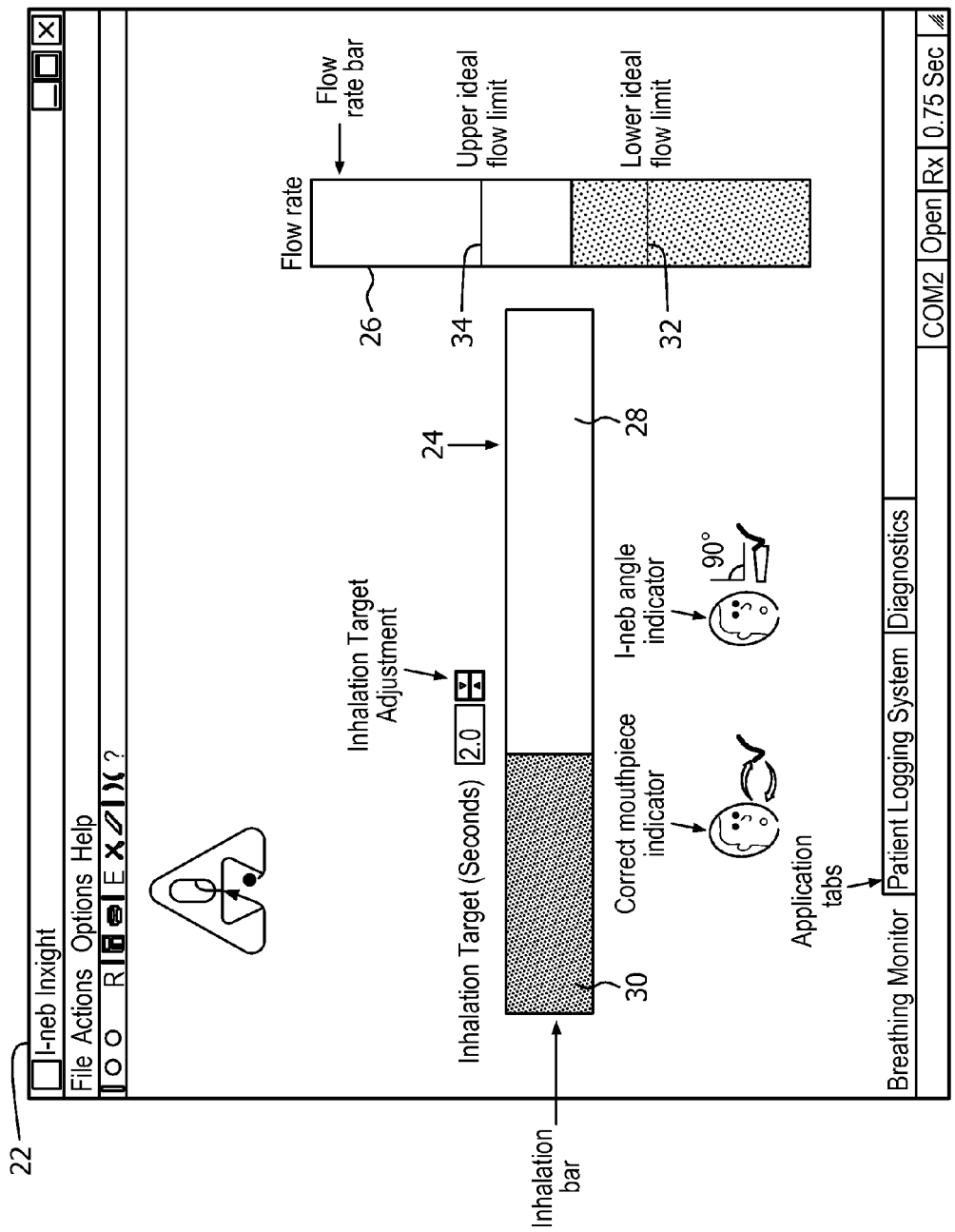
FIG. 3 illustrates a graphical user interface displayed on a display of a client computer platform, according to one or more embodiments of the invention.

By way of non-limiting example, FIG. 3 illustrates a graphical user interface 22 displayed on a display of a client computer platform that is the same as or similar to client computing platform 14 shown in FIG. 1 and described herein. The client computer platform displaying graphical user interface 22 is in operative communication with a drug delivery device that is the same as or similar to drug delivery device 12 shown in FIG. 1 and described herein. As can be seen in FIG. 3, graphical user interface 22 includes an inhalation time display object 24 and an inhalation flow display object 26.

In the embodiment illustrated in FIG. 3, inhalation time display object 24 includes an "empty" rectangle 28. At the beginning of a training inhalation, a colored section 30 formed at one side of the rectangle 28 begins to spread across rectangle 28. The rate at which colored section 30 increases in size corresponds to a target inhalation time such that at the target inhalation time colored section 30 will completely fill in rectangle 28. The target inhalation time may be predetermined, may adjust dynamically based on one or more previous training inhalations, and/or may be set manually by the subject (e.g., as shown in FIG. 3).

In order to train the subject with respect to the proper inhalation flow rate, inhalation flow display object 26 is shown as a gauge having a lower ideal flow demarcation 32 and an upper ideal flow demarcation 34. As the subject inhales through the drug delivery device, the gauge is at least partially colored to a level that corresponds to a current flow rate. The subject is encouraged to keep the flow rate between the lower ideal flow demarcation 32 and the upper ideal flow demarcation 34 for the duration of the inhalation (e.g., for the entire target inhalation time).

During a single training session, graphical user interface 22 may prompt the subject to take a predetermined number of training inhalations. Therapy information is acquired by the drug delivery device during these training inhalations. This therapy information include target inhalation time, instantaneous flow, peak flow, volume, time at ideal inhalation flow, actual inhalation time, and/or other information related to the training inhalations. From the therapy information, the drug delivery device and/or the client computer platform may determine additional metrics related to subject respiration, such as respiratory capacity.

Figure 4:
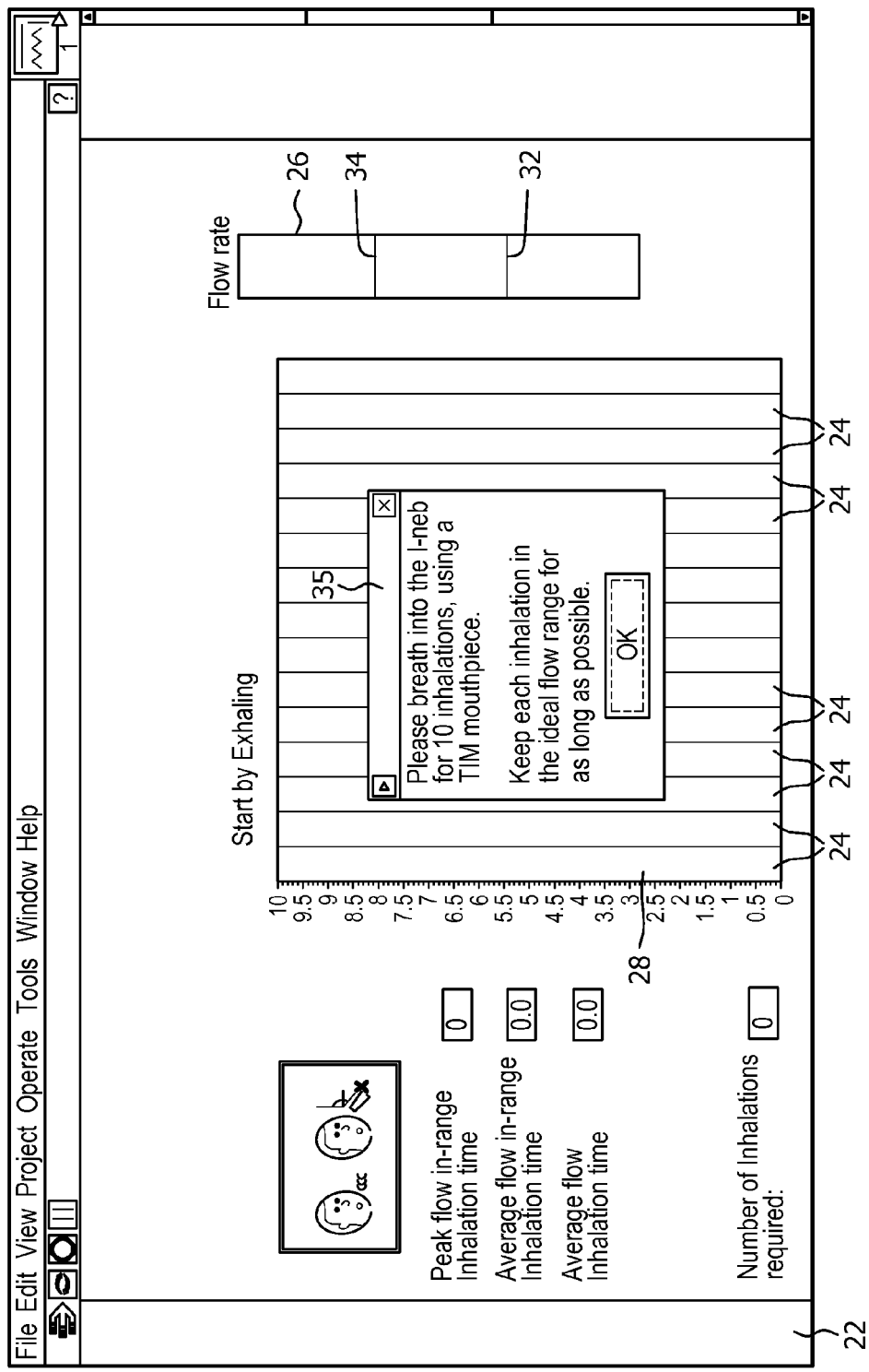
FIG. 4 illustrates a graphical user interface displayed on a display of a client computer platform, according to one or more embodiments of the invention.
Figure 5:
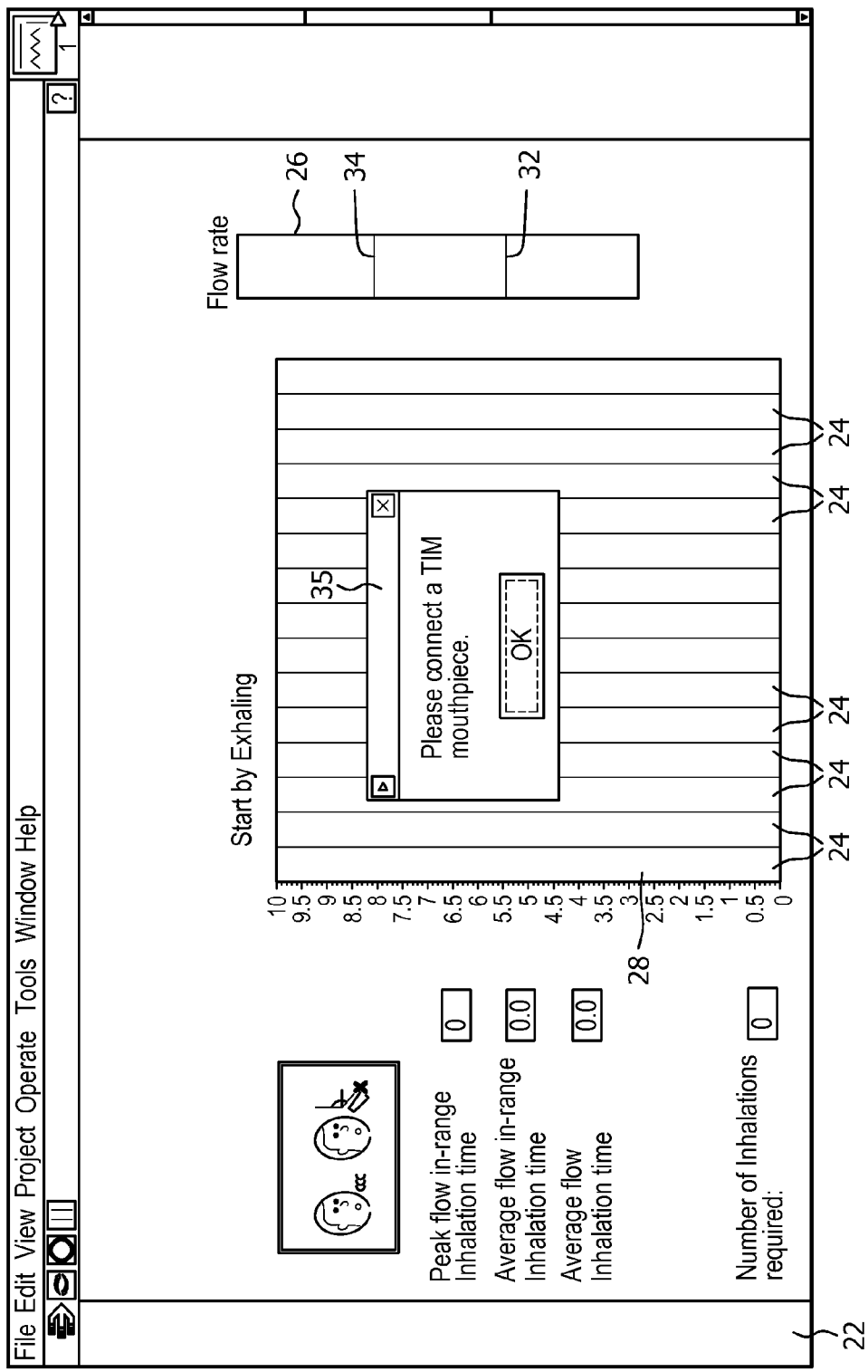
FIG. 5 illustrates a graphical user interface displayed on a display of a client computer platform, according to one or more embodiments of the invention.

FIGS. 4-8 illustrate how, in one embodiment, graphical user interface 22 is implemented to instruct a subject how to inhale during therapy. FIG. 4 shows a view of graphical user interface 22 provided to the subject with an instructional dialogue box 35. The instructional dialogue box 35 provides an initial set of instructions to the subject that provide an overview for the subject of the training session. In the embodiment illustrated in FIG. 4, the instructions indicate that the subject should breath into a drug delivery device (e.g., similar to or the same as drug delivery device 12 shown in FIG. 1 and described herein) for a predetermined number (e.g., 10) inhalations. The instructions further indicate that during each of the inhalations, the subject should attempt to maintain the flow rate of inhalation such that inhalation flow display object 26 is kept between lower ideal flow demarcation 32 and upper ideal flow demarcation 34.

In one embodiment, the drug delivery device includes one or more components (e.g., mouthpiece, spacer, medicament canister, etc.) that can be selectively removed and replaced. This may facilitate the delivery of different types of medicament, different dosages, and/or other differentiations between therapy sessions with the same drug delivery device. The drug delivery device may be capable of automatically detecting its current configuration, and/or the subject may be prompted to configure the drug delivery device for a training session. For example, in the view of graphical user interface 22 shown in FIG. 5, instructional dialogue box 35 provides instructions to the subject to connect a specific type of mouthpiece (La, a TIM mouthpiece) to the drug delivery device for the training session.

Figure 6:
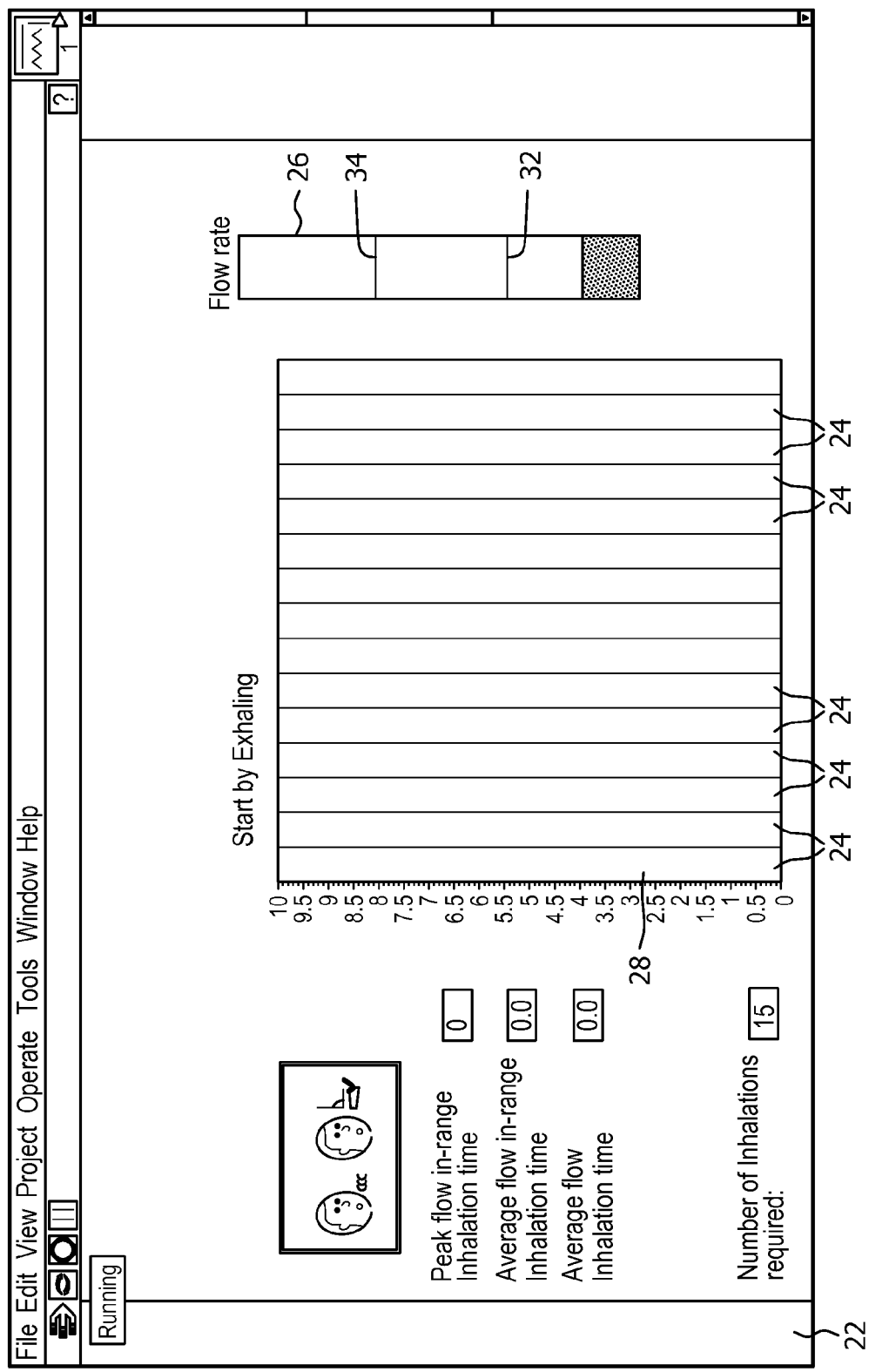
FIG. 6 illustrates a graphical user interface displayed on a display of a client computer platform, according to one or more embodiments of the invention.

FIG. 6 illustrates a view of graphical user interface 22 in which the first inhalation of a training session has been begun, but the flow rate of inhalation of the subject has not yet been raised to between lower ideal flow demarcation 32 and upper ideal flow demarcation 34 on inhalation flow display object 26. As such, in the inhalation time display object 24 corresponding to the first breath, none of rectangle 28 has been colored in (to thereby indicate time spent inhaling).

Figure 7:
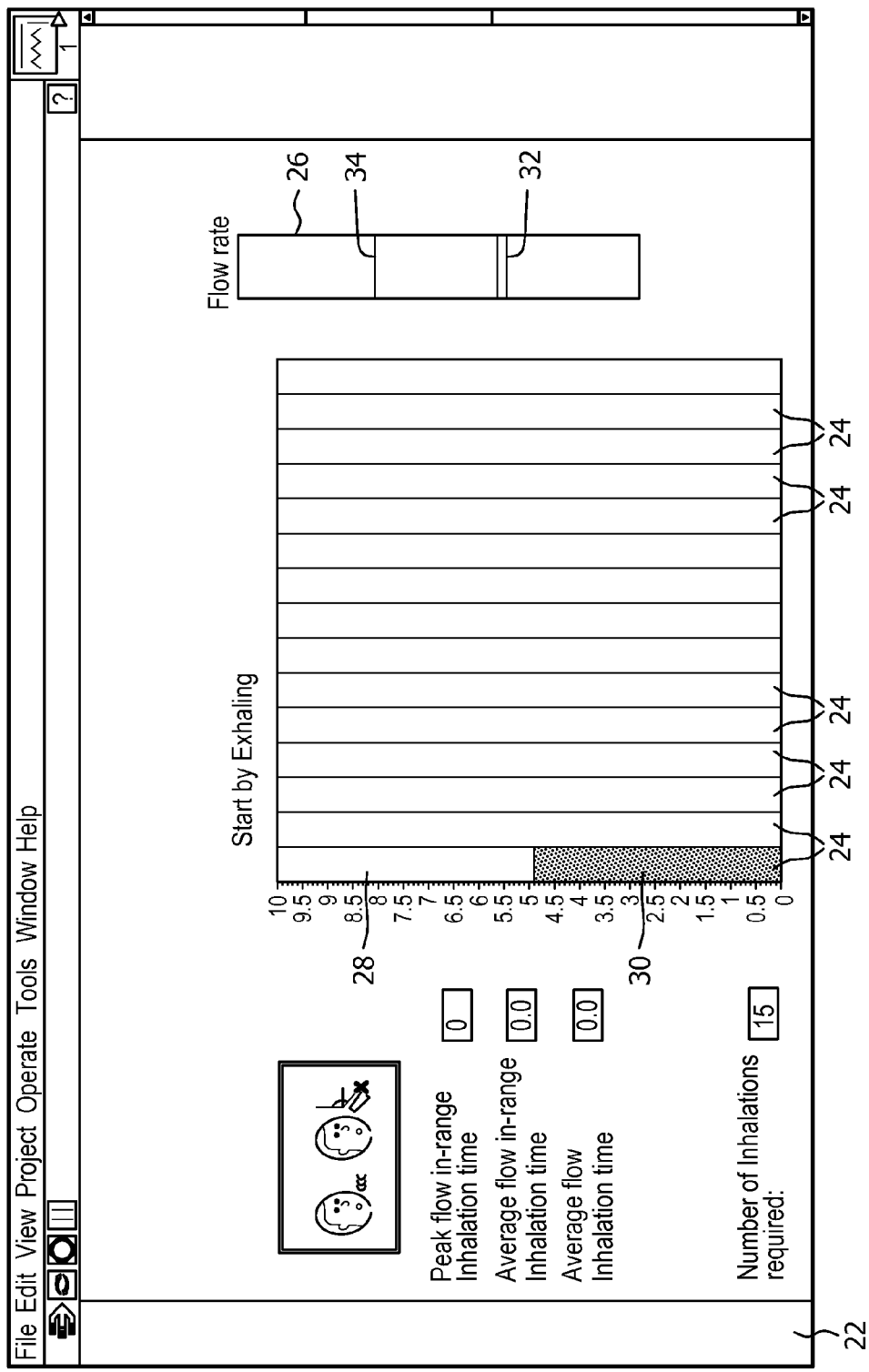
FIG. 7 illustrates a graphical user interface displayed on a display of a client computer platform, according to one or more embodiments of the invention.

FIG. 7 illustrates a view of graphical user interface 22 in which the inhalation flow rate of the subject during the first inhalation has caused inhalation flow display object 26 to rise to between lower ideal flow demarcation 32 and upper ideal flow demarcation 34. As a result, rectangle 28 of inhalation time display object 24 has begun to be filled in by colored section 30 indicating the amount of time that the inhalation flow rate has been between lower ideal flow demarcation 32 and upper ideal flow demarcation 34.

Figure 8:
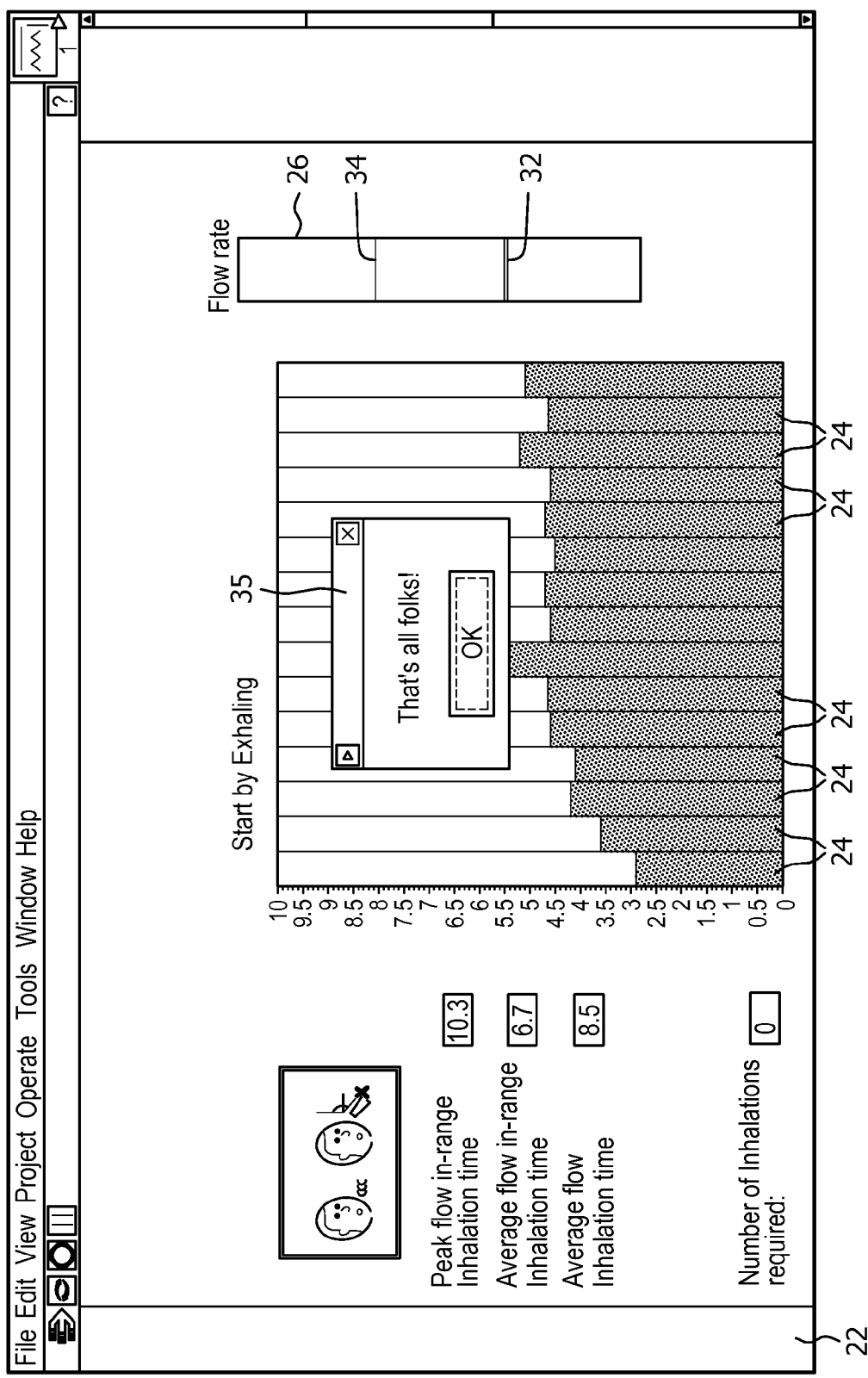
FIG. 8 illustrates a graphical user interface displayed on a display of a client computer platform, according to one or more embodiments of the invention.

As can be seen in FIG. 7, graphical user interface 22 includes a plurality of inhalation time display objects 24 corresponding to separate inhalations during the training session. As that subject finishes the first inhalation, the process described above with respect to the first inhalation and FIGS. 6 and 7 would then be repeated for each successive inhalation and the corresponding inhalation time display object 24 for the course of the training session. FIG. 8 illustrates a view of graphical user interface 22 in which the training session has been completed (see the indications of inhalation length in inhalation time display objects 24), and instructional dialogue box 35 instructs the subject that the training session has been concluded.

It will be appreciated that none of the specific embodiments for providing instructions to the subject on how to breathe during treatment illustrated in FIGS. 3-8 are not intended to be limiting. The information presented in the graphical user interfaces illustrated in FIGS. 3-8, and/or other information relevant to training subjects how to breathe during therapy, may be provided to users in graphical user interfaces formatted differently without departing from the scope of this disclosure.

Similarly, training sessions may be designed differently than described above to determine information related to the respiratory capacity of subjects. By way of non-limiting example, rather than simply having the subjects breathe for as long as they are able, the graphical user interface (or other user interface) may deliver a signal to a subject to end a current inhalation. As was described above, the amount of time that it takes for the subject to react to such a signal (whether delivered during a training session or during the delivery of therapy) may enable a determination of the respiratory capacity of the subject.

Referring back to FIG. 1, client computing platforms 14 are communicatively linked with server 16. Communications between client computing platforms 14 and server 16 may be implemented via a network. This network may include, for example, the Internet and/or an intranet associated with a clinic (or set of clinics), a hospital (or set of hospitals), a research institution, and/or other entities.

Server 16 includes one or more computing platforms configured to serve information to a plurality of client applications being executed on client computing platforms. By way of non-limiting example, server 16 may include a Web server. In one embodiment, server 16 is a dedicated server platform that is solely executing computer modules associated with hosting and serving content. In one embodiment, server 16 is implemented on a computing platform that is performing other types of processing concomitant with the server functionality discussed herein. In this embodiment server 16 may be embodied in a computing platform such as a personal desktop or laptop computer that is configured to perform server functionality. Although server 16 is illustrated in FIG. 1 as an actually physically separate component, in one embodiment, server 16 is a virtual server accessible to client computing platforms 14 and 20 over the communications network(s).

As can be seen in FIG. 1, server 16 includes a processor 36. Processor 36 is configured to provide information processing capabilities in server 16. As such, processor 36 may include one or more of a digital processor, an analog processor, a digital circuit designed to process information, an analog circuit designed to process information, a state machine, and/or other mechanisms for electronically processing information. Although processor 36 is shown in FIG. 1 as a single entity, this is for illustrative purposes only. In some implementations, processor 36 may include a plurality of processing units. These processing units may be physically located within the same device, or processor 36 may represent processing functionality of a plurality of devices (e.g., a plurality of servers) operating in coordination to provide the functionality attributed herein to server 16.

Processor 36 is configured to execute one or more computer program modules. The one or more computer program modules may include one or more of a information acquisition module 38, a users module 40, an subjects module 42, a threshold module 44, a monitor module 46, a user interface module 48, a communications module 50, an alert module 52, a therapy adjustment module 54, and/or other modules. Processor 36 may be configured to execute modules 38, 40 42, 44, 48, 50, 52, and/or 54, by software; hardware; firmware; some combination of software, hardware, and/or firmware; and/or other mechanisms for configuring processing capabilities on processor 36.

It should be appreciated that although modules 38, 40 42, 44, 48, 50, 52, and 54 are illustrated in FIG. 1 as being co-located within a single processing unit, in implementations in which processor 36 includes multiple processing units, one or more of modules 38, 40 42, 44, 48, 50, 52, and/or 54 may be located remotely from the other modules. The description of the functionality provided by the different modules 38, 40 42, 44, 48, 50, 52, and/or 54 set forth below is for illustrative purposes, and is not intended to be limiting, as any of modules 38, 40 42, 44, 48, 50, 52, and/or 54 may provide more or less functionality than is described. For example, one or more of modules 38, 40 42, 44, 48, 50, 52, and/or 54 may be eliminated, and some or all of its functionality may be provided by other ones of modules 38, 40 42, 44, 48, 50, 52, and/or 54. As another example, processor 36 may be configured to execute one or more additional modules that may perform some or all of the functionality attributed below to one of modules 38, 40 42, 44, 48, 50, 52, and/or 54.

The information acquisition module 38 is configured to obtain therapy information from a plurality of drug delivery devices, including drug delivery devices 12. In one embodiment, this includes communicating with client computing platforms 14 to receive therapy information that has been transferred from drug delivery devices 12 to client computing platforms 14, respectively. The therapy information obtained by information acquisition module 38 from client computing platforms 14 is received by information acquisition module 38 over the communications network linking server 16 with client computing platform 14. The transfer of therapy information from client computing platform 14 to information acquisition module 38 over the communications network may be initiated automatically (e.g., after additional therapy information has been obtained by client computing platform 14 from drug delivery device 12, at predetermined intervals, etc.), or manually by the subject via a command input to client computing platform 14.

The users module 40 is configured to manage one or more user profiles of users that are provided with access to therapy information obtained by server 16 from drug delivery devices 12. As used herein the term "user" may include a caregiver, a researcher, an administrator, and/or other individuals that should be provided with access to therapy information associated with a plurality of the subjects using drug delivery devices 12. The user profiles may include one or more of identification information (e.g., user ID, etc.) that enables the users to be identified and/or associated with particular user profiles, authentication information (e.g., login, password, etc.) that enables the users to be authenticated to server 16, configuration preferences associated with the users, and/or other information associated with the individual users.

It will be appreciated that the two drug delivery device 12 are not the only drug delivery devices for which server 16 receives therapy information. For example, in FIG. 1, additional drug delivery devices (not shown) are also communicatively linked with server 16 (e.g., via corresponding client computing platforms). In one embodiment, the information related to individual users included in the user profiles managed by users module 40 includes access privileges that indicate which drug delivery devices the individual users should be given access to. The access privileges may even indicate specific types of therapy information for which access should be given to a given user (e.g., information related to performance efficiency or effectiveness of a device, but not information related to patient respiratory capacity, treatment, and/or compliance).

The subjects module 42 is configured to manage a plurality of subject profiles that correspond to the subjects for which therapy information is obtained by information acquisition module 38. The subject profile corresponding to a given subject includes one or more of identification information identifying the subject (e.g., name, patient or subject number, etc.) and the therapy information obtained for the given subject. The subject profile corresponding to the given subject may include information related to which users should receive access to therapy information associated with the given subject.

The threshold module 44 is configured to set one or more thresholds for a first breathing parameter and/or other breathing parameters individually for subjects while receiving aerosolized medicament from drug delivery devices 12. By way of non-limiting example, the first breathing parameter may include one or more of an inhalation time, an estimated respiratory capacity, an inhalation volume, an inhalation flow, an breath period or frequency, and/or other breathing parameters. The one or more thresholds for the first breathing parameter determined for a given subject are determined based on therapy information received by information acquisition module 38 from the drug delivery device 12 corresponding to the given subject.

In one embodiment, the first breathing parameter is related to inhalation duration. For instance, the first breathing parameter may be an average or median inhalation duration during the therapy session or group of therapy sessions, a total amount of time spent inhaling during a therapy session or group of therapy sessions, a respiratory capacity estimated from therapy information during a therapy session or group of therapy sessions, and/or other parameters related to inhalation duration. The one or more thresholds for the first breathing parameter in this embodiment are determined based on information related to respiratory capacity obtained by information acquisition module 38. For instance, based on a baseline respiratory capacity determined based on the subjects performance during a training session (e.g., the training sessions described above with respect to FIGS. 3-8), the one or more thresholds may be determined. This may include setting the one or more thresholds for inhalation duration at percentages of the baseline respiratory capacity. As a non-limiting example, a first threshold may be set at or near 80% of the baseline respiratory capacity, and/or a second threshold may be set at or near 50% of the baseline respiratory capacity. It will be appreciated that more or alternative thresholds may be set at or near other percentage levels (e.g., 75%, 70%, 65%, 60%, 55%, etc.).

The monitor module 46 is configured to monitor the therapy received by the first subject by comparing the first breathing parameter during therapy sessions with the one or more thresholds set by threshold module 44. For example, if the first breathing parameter indicates that inhalation duration is maintained above the first threshold, this may indicate that the therapy is having effect, and that the subject is gaining or at least maintaining respiratory capacity. If the first breathing parameter indicates that inhalation duration is dropping and falls below the first threshold, this may indicate one or more of: (i) the therapy is not having the planned effect and the subject is losing respiratory capacity, (ii) the subject is not breathing properly during therapy sessions and should be retrained (e.g., through a training session as described above with respect to FIGS. 3-8), or (iii) the drug delivery device used by the subject is not functioning properly and may need to be serviced and/or replaced. If the first breathing parameter indicates that inhalation duration is dropping and falls below the second threshold, this may indicate a more urgent physiological deterioration than the first breathing parameter indicating that inhalation duration has breached only the first threshold. If the second threshold is broken, it may be imperative that one or more of the following are initiated: (i) additional therapeutic and/or diagnostic steps, (ii) a retraining of the subject (e.g., through a training session as described above with respect to FIGS. 3-8) followed by improved performance during therapy sessions, (iii) service and/or replacement of the drug delivery device implemented by the subject.

It will be appreciated that the description above of monitor module 46 monitoring the inhalation duration of the subject based solely on comparison with thresholds determined by threshold module 44 is not intended to be limiting. Other types of evaluations may be performed on the first breathing parameter and/or other breathing parameters of the subject during therapy sessions to monitor the efficacy of therapy, the health of the subject, the maintenance of the drug delivery device, and/or other aspects of the therapy received by the subject without departing from the scope of this disclosure.

The user interface module 48 is configured to generate a definition of a user interface for a user that enables the user to selectively view therapy information obtained by information acquisition module 38, information related to thresholds determined by threshold module 44, information generated by monitor module 46 in monitoring the therapy of subjects, and/or other information. This includes enabling a user to select a specific subjects or set of subjects, and to view information associated with the specific subject or set of subjects based on the selection. The user interface defined by the definition generated by user interface module 48 further enables a user to select an information type, analysis based on the therapy information, a specific view of selected information and/or analysis; and to view the selected information type and/or analysis in the selected view.

In one embodiment, the definition of the user interface generated by user interface module 48 includes a definition of a web page that can be viewed in a Web browser on a client computing platform. The definition of the web page may include, for example, HTML, dHTML, XML, JAVA, Flash, and/or information encoded in other formats that are readable by a Web browser. In one embodiment, the definition of the user interface generated by user interface module 48 is generated for a more specialized client side application. For example, the client side application may already include views for selectively viewing therapy information, and the definition of the user interface generated by user interface module 48 may include merely values for the therapy information that is viewable within a given view provided by the client side application. In this embodiment, the client side application receives the values for the therapy information included in the definition of the user interface that inserts some or all of the values (as appropriate) into the corresponding portions of a view.

Figure 9:
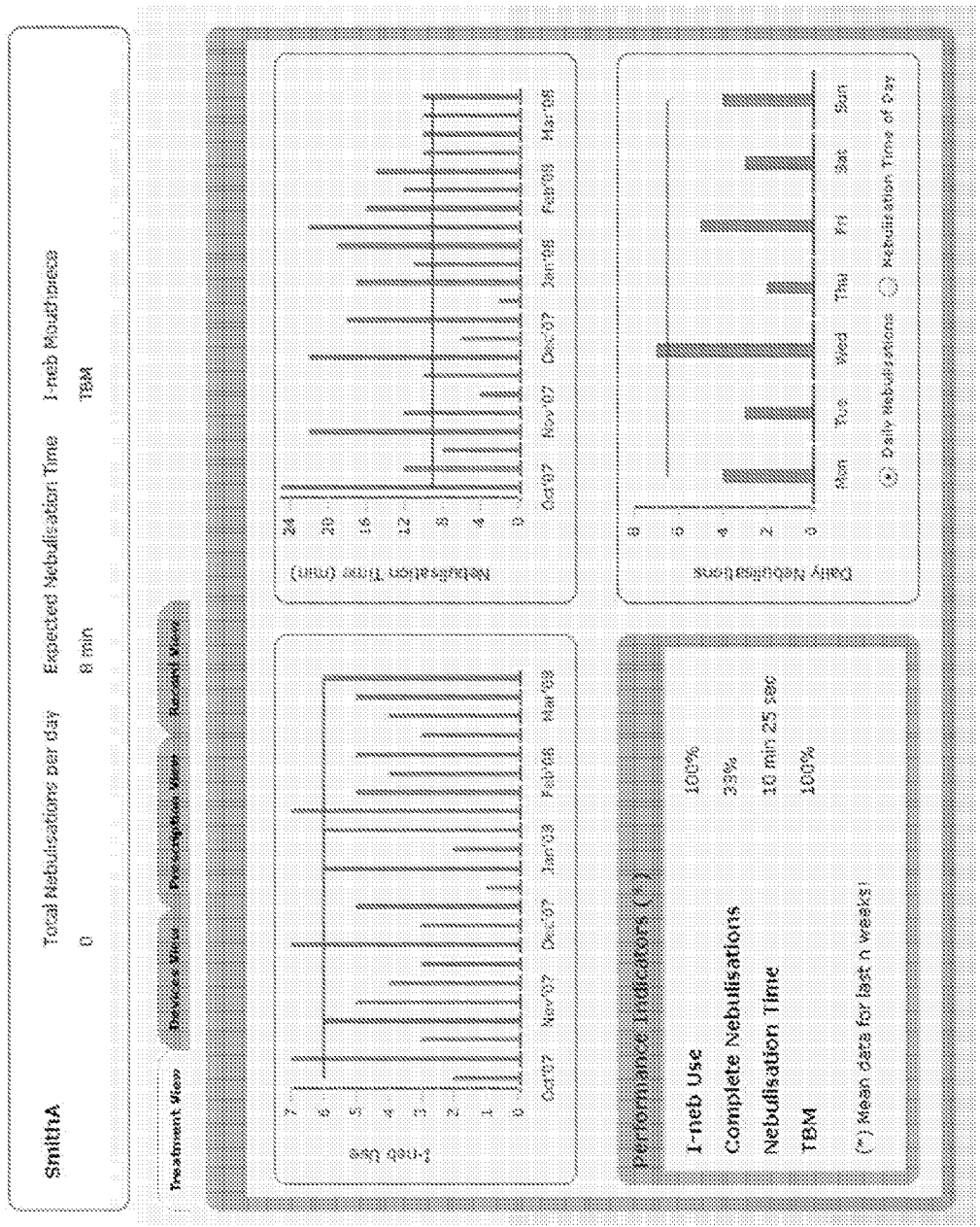
FIG. 9 illustrates a graphical user interface displayed on a display of a client computer platform, according to one or more embodiments of the invention.

By way of illustration, FIG. 9 shows a view of the user interface defined by user interface module 48 that includes therapy information related to subject compliance to a treatment regime. This view may be referred to as a "treatment view." As can be seen in FIG. 9, the treatment view provides the user with information about the frequency and/or duration of treatments received by a subject or group of subjects, and/or other information.

Figure 10:
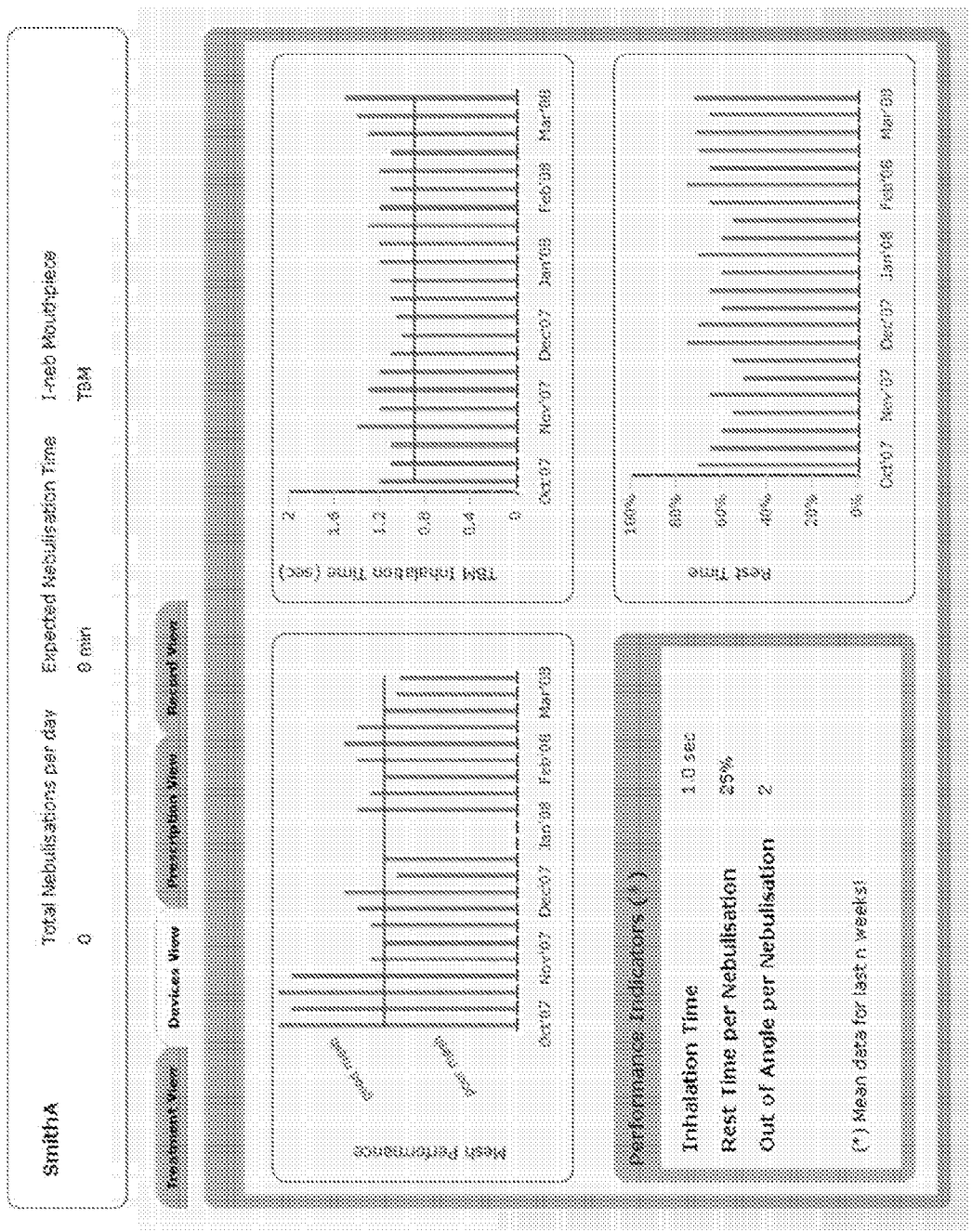
FIG. 10 illustrates a graphical user interface displayed on a display of a client computer platform, according to one or more embodiments of the invention.

Similarly, FIG. 10 illustrates an embodiment of the user interface defined by user interface module 48 in which the user interface includes a view that presents therapy information to the user related to the performance of a drug delivery device used by a patient or group of patients. This view may be referred to as a "device view." The device view includes information related to metrics that quantify drug delivery device performance.

Other views that may be included in the user interface may include one or more of a prescription view, a record view, a subject grouping view, a respiratory capacity view, and/or other views. The prescription view includes information related to the therapy regime that has been prescribed for a subject or group of subjects. The record view includes information related to historical device usage and/or respiratory function of a subject or group of subjects. The subject grouping view enables the user to view, create, and/or manipulate groupings of subjects. The subject groupings may be established based on one or more of demographic information (e.g., age, ethnicity, sex, geographic location, education, socioeconomic classification, and/or other demographic information), medical condition, medicament received, therapy regime prescribed, respiratory capacity, and/or other information. This grouping may be done manually by the user and/or automatically by server 16.

Returning to FIG. 1, in one embodiment, the user interface defined by user interface module 48 enables the user to interact with the thresholds defined by threshold module 44. This interaction may occur on a per subject basis, across a group or set of subjects, and/or for all subjects that the user has access to. The interactivity provided to the user by the user interface includes the ability to input or adjust percentages of respiratory capacity at which thresholds are set, the ability to input or adjust the number of thresholds, and/or other interactive functionality.

The communications module 50 is configured to provide the definition of the user interface generated by user interface module 48 to the user. In one embodiment, communications module 48 accomplishes this by serving the user interface to client computing platform 20 associated with the user. The client computing platform 20 may include one or more of a laptop computer, a desktop computer, a netbook, a smartphone, and/or other client computing platforms. The communications module 50 may serve the user interface to client computing platform 20 over a network. This network may include the Internet and/or an intranet associated with a clinic (or set of clinics), a hospital (or set of hospitals), or other entities. In order to view the defined user interface, client computing platform 20 may implement a versatile client application, like a web browser, to render the user interface based on the communication from communications module 20. As was mentioned above, in one embodiment, rather than a versatile client application like a web browser, client computing platform 20 may execute a client application that is specifically designed for viewing the user interface defined by communications module 50.

In one embodiment, the user interface defined by user interface module 48 enables the user to input communication directed toward a subject or group of subjects. This communication is then distributed by communications module 48 to the subject or group of subjects. The communication may be distributed to the subject or group of subjects via their drug delivery devices (e.g., via drug delivery device 12 by way of client computing platform 14), via one or more client computing devices associated with the subject or group of subjects, and/or via other communication devices associated with the subject or group of subjects (e.g., via SMS message, via voicemail, via automated phone call, etc.). These communications may include messages selected by the user from a predefined set of communications indicating action that the patient or group of patients should with respect to their drug delivery device(s), adjustments that should be made to the treatment regime prescribed for the patient or group of patients, adjustments that should be made by the patient or group of patients to respiration during treatment, promptings to participate in a training session, communication that results in the automatic initiation of a training session, and/or other messages. The user interface may present a set of communications to the user for transmission to the subject(s) based on analysis performed by monitor module 46 (e.g., based on comparisons of breathing parameter(s) during treatment with threshold(s)).

In one embodiment, communications module 50 further enables subjects to transmit communications back to the user. For example, communications module 50 may be configured to receive communications input by a subject to drug delivery device 12 and/or client computing platform 14, and to provide such communication to the appropriate user (e.g., via client computing platform 14). These communications may be in response to communications received from the user (e.g., confirming a change and/or action indicated in a communication from the user has been made and/or taken), or may be instigated entirely by the subject.

The alert module 52 is configured to generate alerts to the users related to the therapy information obtained by information acquisition module 38. For example, alert module 52 may be configured to generate alerts to a user responsive to the first breathing parameter of a given subject breaching a threshold set for the given subject by threshold module 44. In this example, the breach of the threshold may be determined by monitor module 46, and the generation of the alert by alert module 52 may be responsive to this determination.

The alerts generated by alert module 52 may be provided to the user via the user interface defined by user interface module 48 and communicated to the subject via communications module 50. In one embodiment, the alerts generated by alert module 52 are delivered to subjects by communications module 50 via communications media other the user interface defined by user interface module 48. For example, communications module 50 may transmit the alerts to the subjects via one or more of SMS and/or text message, email, other electronic text-based communication, voicemail, automated telephone call, and/or other communications media.

The therapy adjustment module 54 may be configured to adjust one or more parameters of the therapy regimes prescribed for individual subjects. Such adjustments may include adjustments to medicament dosage, medicament composition, therapy session duration, therapy session frequency, and/or other parameters. These adjustments may be made automatically based on analysis performed by monitor module 46 and/or manually by a user. The user may be provided with the ability to manually adjust the one or more parameters of the therapy regimes for a given subject via the user interface defined by user interface module 48. Adjustments to parameters of the therapy regime for a given subject may be communicated to the given subject by communications module 50 via drug delivery device 12 and/or client computing platform 14.

Figure 11:
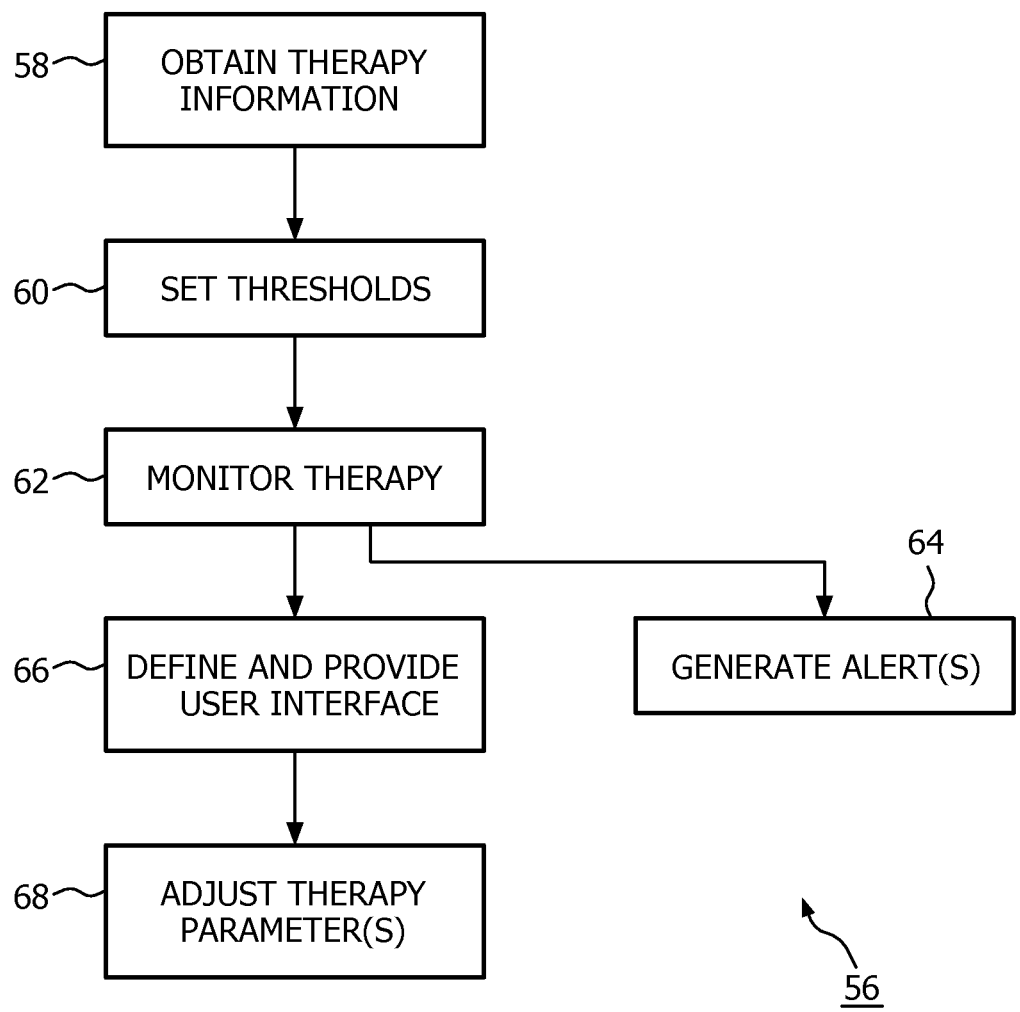
FIG. 11 illustrates a flow-chart of a method of remotely monitoring and/or managing therapy regimes of a plurality of subjects, in accordance with one or more embodiments of the invention.

FIG. 11 illustrates a method 56 of monitoring and/or managing the therapy of a plurality of subjects, wherein the therapy includes the delivery of aerosolized medicament with drug delivery devices. The operations of method 56 presented below are intended to be illustrative. In some embodiments, method 56 may be accomplished with one or more additional operations not described, and/or without one or more of the operations discussed. Additionally, the order in which the operations of method 56 are illustrated in FIG. 11 and described below is not intended to be limiting.

In some embodiments, method 56 may be implemented by a server including one or more processors (e.g., a digital processor, an analog processor, a digital circuit designed to process information, an analog circuit designed to process information, a state machine, and/or other mechanisms for electronically processing information) configured to execute one or more computer program modules. The one or more processors may include one or more devices executing some or all of the operations of method 56 in response to instructions stored electronically on an electronic storage medium. The one or more processors may include one or more devices configured through hardware, firmware, and/or software to be specifically designed for execution of one or more of the operations of method 56.

At an operation 58, therapy information is obtained for a plurality of subjects. The plurality of subjects includes information related to the respiratory capacities of the individual subjects and one or more breathing parameters of the individual subjects during the delivery of aerosolized medicament. In one embodiment, operation 58 is performed by a information acquisition module that is the same as or similar to information acquisition module 38 (shown in FIG. 1 and described above).

At an operation 60, one or more thresholds are set for a first breathing parameter for the individual subjects based on the information related to respiratory capacities of the subjects obtained at operation 58. In one embodiment, operation 60 is performed by a threshold module that is the same as or similar to threshold module 44 (shown in FIG. 1 and described above).

At an operation 62, the therapy of the individual subjects is monitored. The therapy of the individual subjects may be monitored by comparing the thresholds set at operation 60 to the one or more breathing parameters of the subjects during the delivery of aerosolized medicament that is obtained at operation 58. In one embodiment, operation 62 is performed by a monitor module that is the same as or similar to monitor module 46 (shown in FIG. 1 and described above).

At an operation 64, one or more alerts are generated to a user based on the monitoring of the therapy of the subjects that is performed at operation 62. The one or more alerts may be generated responsive to a breathing parameter of one or more of the subjects during delivery of aerosolized medicament breaching one or more of the thresholds set at operation 60. In one embodiment, operation 64 is performed by alert module that is the same as or similar to alert module 52 (shown in FIG. 1 and described above).

At an operation 66, a user interface is defined and provided to the user. The user interface enables the user to selectively view, for individual subjects and/or groups of subjects, therapy information and the one or more thresholds set at operation 60. In one embodiment, operation 66 is performed by a user interface module and a communications module that are the same as or similar to user interface module 48 and communications module 50, respectively (shown in FIG. 1 and described above).

At an operation 68, one or more parameters of the therapy regime(s) prescribed for one or more of the subjects are adjusted. The parameters of a given therapy regime may be adjusted based on the therapy information obtained at operation 58 for the user that corresponds to the given therapy regime, and/or the thresholds set at operation 60 for the user that corresponds to the given therapy regime. Adjustments to parameters of the therapy regime(s) made at operation 68 may be made automatically (e.g., based on the monitoring performed at operation 62) and/or manually (e.g., entered by the user via the user interface defined and provided at operation 66). In one embodiment, operation 68 is performed by a therapy adjustment module that is the same as or similar to therapy adjustment module 54 (shown in FIG. 1 and described above).

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A system configured to remotely monitor therapy of a plurality of subjects, wherein the therapy includes delivery of aerosolized medicament, the system comprising:
   one or more hardware processors configured by machine-readable instructions to:
      obtain, over a communications network, therapy information for a plurality of subjects, wherein the plurality of subjects comprise at least a first subject and a second subject, and wherein therapy information for a given subject includes information related to a respiratory capacity of the given subject and information conveying one or more breathing parameters of the given subject during the delivery of the aerosolized medicament;

automatically set one or more first thresholds for a first breathing parameter for the first subject during delivery of aerosolized medicament to the first subject based on first information related to a first respiratory capacity of the first subject, and automatically set one or more second thresholds for a second breathing parameter for the second subject during delivery of aerosolized medicament to the second subject based on second information related to a second respiratory capacity of the second subject;

cause a first user interface to be displayed to the first subject, prior to the delivery of aerosolized medicament to the first subject, to present first visual cues in separate fields of a first single view of the first user interface that facilitate a first training inhalation by the first subject such that a first inhalation time of the first training inhalation being within a first target inhalation time range is displayed in a first field of the first single view, and a first inhalation flow rate of the first training inhalation being within a first target inhalation flow rate range is displayed in a second field of the first single view;

cause a second user interface to be displayed to the second subject, prior to delivery of aerosolized medicament to the second subject, to present second visual cues in separate fields of a second single view of the second user interface that facilitate a second training inhalation by the second subject such that a second inhalation time of the second training inhalation being within a second target inhalation time range is displayed in a third field of the second single view, and a second inhalation flow rate of the second training inhalation being within a second target inhalation flow rate range is displayed in a fourth field of the second single view;

monitor the therapy received by the first subject by comparing the first breathing parameter during delivery of aerosolized medicament, as conveyed by the therapy information for the first subject, with the one or more first thresholds;

monitor the therapy received by the second subject by comparing the second breathing parameter during the delivery of the aerosolized medicament, as conveyed by the therapy information for the second subject, with the one or more second thresholds;

responsive to the first breathing parameter breaching at least one of the one or more first thresholds, (i) cause the first user interface to be redisplayed to the first subject to facilitate at least one first additional training inhalation by the first subject, (ii) set one or more new first thresholds for the first breathing parameter based, at least in part, on a first breathing performance during the at least one first additional training inhalation, and (iii) adjust one or more first therapy regime parameters of the first subject based on the first breathing performance during the at least one first additional training inhalation, the one or more first therapy regime parameters including one or more of a medicament dosage, a medicament composition, a therapy session duration, or a therapy session frequency; and responsive to the second breathing parameter breaching at least one of the one or more second thresholds, (i) cause the first user interface to be redisplayed to the second subject to facilitate at least one second additional training inhalation by the second subject, (ii) set one or more new second thresholds for the second breathing parameter based, at least in part, on a second breathing performance during the at least one second additional training inhalation, and (iii) adjust one or more second therapy regime parameters of the second subject based on the second breathing performance during the at least one second additional training inhalation, the one or more second therapy regime parameters including one or more of a medicament dosage, a medicament composition, a therapy session duration, or a therapy session frequency.

2. The system of claim 1, wherein the one or more hardware processors are further configured to generate a definition of a third user interface that enables a user to selectively view the therapy information and the one or more first thresholds and the one or more second thresholds.

3. The system of claim 2, wherein the third user interface provides the user with the ability to adjust at least one of the one or more first thresholds, and provides the user with the ability to adjust at least one of the one or more second thresholds.

4. The system of claim 3, wherein:
the at least one of the one or more first thresholds being adjusted comprises adjusting a first percentage of the first respiratory capacity; and
the at least one of the one or more second thresholds being adjusted comprises adjusting a second percentage of the second respiratory capacity.

5. The system of claim 2, wherein the third user interface provides the user with the ability to input adjustments to the therapy regime of the first subject and with the ability to input adjustments to the therapy regime second subject, and wherein the one or more hardware processors are further configured to communicate, over the communications network, any adjustments to the therapy regimes of the first subject or the second subject to the appropriate one of the first subject or the second subject.

6. The system of claim 1, wherein the one or more hardware processors are further configured to (i) to generate, responsive to the first breathing parameter breaching at least one of the one or more first thresholds, a first alert to the user, and (ii) to generate, responsive to the second breathing parameter breaching at least one of the one or more second thresholds, a second alert to the user.

7. The system of claim 1, wherein:
at least one of the one or more first thresholds are set as a first percentage of a first baseline respiratory capacity of the first subject; and
at least one of the one or more second thresholds are set as a second percentage of a second baseline respiratory capacity of the second subject.

8. The method of claim 1, wherein:
at least one of the one or more first thresholds are set as a first percentage of a first baseline respiratory capacity of the first subject; and
at least one of the one or more second thresholds are set as a second percentage of a second baseline respiratory capacity of the second subject.

9. A computer implemented method of remotely monitoring therapy of a plurality of subjects, wherein the therapy includes the delivery of aerosolized medicament, the method comprising:
obtaining, over a communications network, therapy information for a plurality of subjects, wherein the plurality of subjects comprise at least a first subject and a second subject, and wherein therapy information for a given subject includes information related to a respiratory capacity of the given subject and information conveying one or more breathing parameters of the given subject during the delivery of aerosolized medicament;

automatically setting one or more first thresholds for a first breathing parameter for the first subject during delivery of aerosolized medicament to the first subject based on the obtained first information related to a first respiratory capacity of the first subject;

automatically setting one or more second thresholds for a second breathing parameter for the second subject during delivery of aerosolized medicament to the second subject based on the obtained second information related to a second respiratory capacity of the second subject;

causing a first user interface to be displayed to the first subject, prior to delivery of aerosolized medicament to the first subject, to present first visual cues in separate fields of a first single view of the first user interface that facilitate a first training inhalation by the first subject such that a first inhalation time of the first training inhalation being within a first target inhalation time range is displayed in a first field of the first single view, and a first inhalation flow rate of the first training inhalation being within a first target inhalation flow rate range is displayed in a second field of the first single view;

causing a second user interface to be displayed to the second subject, prior to delivery of aerosolized medicament to the second subject, to present second visual cues in separate fields of a second single view of the second user interface that facilitate a second training inhalation by the second subject such that a second inhalation time of the second training inhalation being within a second target inhalation time range is displayed in a third field of the second single view, and a second inhalation flow rate of the second training inhalation being within a second target inhalation flow rate range is displayed in a fourth field of the second single view;

monitoring the therapy received by the first subject by comparing the first breathing parameter during delivery of aerosolized medicament, as conveyed by the therapy information for the first subject, with the one or more first thresholds;

monitoring the therapy received by the second subject by comparing the second breathing parameter during the delivery of aerosolized medicament, as conveyed by the therapy information for the second subject, with the one or more second thresholds;

responsive to the first breathing parameter for the first subject breaching at least one of the one or more first thresholds , (i) causing the first user interface to be redisplayed to the first subject to facilitate at least one first additional training inhalation by the first subject, (ii) setting one or more new first thresholds for the first breathing parameter based, at least in part, on a first breathing performance during the at least one first additional training inhalation by the first subject, and (iii) adjusting one or more first therapy regime parameters of the first subject based on the first breathing performance during the at least one first additional training inhalation, the one or more first therapy regime parameters including one or more of a medicament dosage, a medicament composition, a therapy session duration, or a therapy session frequency; and responsive to the second breathing parameter breaching at least one of the one or more second thresholds, (i) causing the first user interface to be redisplayed to the second subject to facilitate at least one second additional training inhalation by the second subject, (ii) setting one or more new second thresholds for the second breathing parameter based, at least in part, on the second breathing performance during the at least one second additional training inhalation, and (iii) adjusting one or more second therapy regime parameters of the second subject based on the second breathing performance during the at least one second additional training inhalation, the one or more second therapy regime parameters including one or more of a medicament dosage, a medicament composition, a therapy session duration, or a therapy session frequency.

10. The method of claim 9, further comprising generating a definition of a third user interface that enables a user to selectively view the therapy information and the one or more first thresholds and the one or more second thresholds.

11. The method of claim 10, wherein the third user interface is configured to provide the user with the ability to adjust at least one of the one or more first thresholds, and provides the user with the ability to adjust at least one of the one or more second thresholds.

12. The method of claim 11, wherein:
the at least one of the one or more first thresholds being adjusted comprises adjusting a first percentage of the first respiratory capacity; and
the at least one of the one or more second thresholds being adjusted comprises adjusting a second percentage of the second respiratory capacity.

13. The method of claim 10, wherein the third user interface is configured to provide the user with the ability to input adjustments to the therapy regime of the first subject and with the ability to input adjustments to the therapy regime second subject, and wherein the method further comprises communicating, over the communications network, any adjustments to the therapy regimes of the first subject or the second subject made by the user to the appropriate one of the first subject or the second subject.

14. The method of claim 9, further comprising:
generating, responsive to the first breathing parameter breaching at least one of the one or more first thresholds, a first alert to the user; and
generating, responsive to the second breathing parameter breaching at least one of the one or more second thresholds, a second alert to the user.

15. A system configured to remotely monitor therapy of a plurality of subjects, wherein the therapy includes the delivery of aerosolized medicament, the system comprising:
means for obtaining, over a communications network, therapy information for a plurality of subjects, wherein the plurality of subjects comprise a first subject and a second subject, and wherein therapy information for a given subject includes information related to a respiratory capacity of the given subject and information conveying one or more breathing parameters of the given subject during the delivery of the aerosolized medicament;
means for automatically setting one or more first thresholds for a first breathing parameter for the first subject during delivery of aerosolized medicament to the first subject based on the obtained first information related to a first respiratory capacity of the first subject;

means for automatically setting one or more second thresholds for the first breathing parameter for the second subject during delivery of aerosolized medicament to the second subject based on the obtained second information related to a second respiratory capacity of the second subject;

means for causing a first user interface to be displayed to the first subject, prior to delivery of aerosolized medicament to the first subject, to present first visual cues in separate fields of a first single view of the first user interface that facilitate a first training inhalation by the first subject such that a first inhalation time of the first training inhalation being within a first target inhalation time range is displayed in a first field of the first single view, and a first inhalation flow rate of the first training inhalation being within a first target inhalation flow rate range is displayed in a second field of the first single view;

means for causing a second user interface to be displayed to the second subject, prior to delivery of aerosolized medicament to the second subject, to present second visual cues in separate fields of a second single view of the second user interface that facilitate a second training inhalation by the second subject such that a second inhalation time of the second training inhalation being within the second target inhalation time range is displayed in a third field of the second single view of the second user interface, and a second inhalation flow rate of the second training inhalation being within a second target inhalation flow rate range is displayed in a fourth field of the second single view;

means for monitoring the therapy received by the first subject by comparing the first breathing parameter during delivery of aerosolized medicament, as conveyed by the therapy information for the first subject, with the one or more first thresholds;

means for monitoring the therapy received by the second subject by comparing the second breathing parameter during the delivery of aerosolized medicament, as conveyed by the therapy information for the second subject, with the one or more second thresholds;

responsive to the first breathing parameter breaching at least one of the one or more first thresholds, (i) means for causing the first user interface to be redisplayed to the first subject to facilitate at least one first additional training inhalation by the first subject, (ii) means for setting one or more new first thresholds for the first breathing parameter based, at least in part, on a first breathing performance during the at least one first additional training inhalation, and (iii) means for adjusting one or more first therapy regime parameters of the first subject based on the first breathing performance during the at least one first additional training inhalation, the one or more first therapy regime parameters including one or more of a medicament dosage, a medicament composition, a therapy session duration, or a therapy session frequency; and responsive to the second breathing parameter breaching at least one of the one or more second thresholds, (i) means for causing the first user interface to be redisplayed to the second subject to facilitate at least one second additional training inhalation by the second subject, (ii) means for setting one or more new second thresholds for the second breathing parameter based, at least in part, on the second breathing performance during the at least one second additional training inhalation, and (iii) means for adjusting one or more second therapy regime parameters of the second subject based on the second breathing performance during the at least one second additional training inhalation, the one or more second therapy regime parameters including one or more of a medicament dosage, a medicament composition, a therapy session duration, or a therapy session frequency.

16. The system of claim 15, further comprising means for generating a definition of a third user interface that enables a user to selectively view therapy information and the one or more first thresholds and the one or more second thresholds.

17. The system of claim 16, wherein the third user interface is configured to provide the user with the ability to adjust at least one of the one or more first thresholds, and provides the user with the ability to adjust at least one of the one or more second thresholds.

18. The system of claim 17, wherein:

the at least one of the one or more first thresholds being adjusted comprises adjusting a first percentage of the first respiratory capacity; and the at least one of the one or more second thresholds being adjusted comprises adjusting a second percentage of the second respiratory capacity.

19. The system of claim 16, wherein the third user interface is configured to provide the user with the ability to input adjustments to the therapy regime of the first subject and with the ability to input adjustments to the therapy regime of the second subject, and wherein the system further comprises means for communicating, over the communications network, any adjustments to the therapy regimes of the first subject or the second subject made by the user to the appropriate one of the first subject or the second subject.

20. The system of claim 15, further comprising:

means for generating, responsive to the first breathing parameter breaching at least one of the one or more first thresholds, a first alert to the user; and means for generating, responsive to the second breathing parameter breaching at least one of the one or more second thresholds, a second alert to the user.

21. The system of claim 15, wherein:

at least one of the one or more first thresholds are set as a first percentage of a first baseline respiratory capacity of the first subject; and at least one of the one or more second thresholds are set as a second percentage of a second baseline respiratory capacity of the second subject.

* * * * *